United States Patent [19]

Plevy

[11] Patent Number: 4,740,368
[45] Date of Patent: Apr. 26, 1988

[54] AMYLASE CONTAINING BREATH CLEANSING CONFECTION

[76] Inventor: Donald J. Plevy, 201 NW. 82nd St., Ste. 305, Plantation, Fla. 33324

[21] Appl. No.: 807,801

[22] Filed: Dec. 11, 1985

[51] Int. Cl.$^4$ .......................... A61K 9/68; A61K 7/28; A61K 37/48
[52] U.S. Cl. ...................... 424/48; 424/50; 424/94.61; 426/3
[58] Field of Search .................. 424/48, 50; 426/3–5, 426/94, 61

[56] References Cited

U.S. PATENT DOCUMENTS

| | | |
|---|---|---|
| 3,574,824 | 4/1971 | Echeandia et al. ............... 424/50 |
| 3,751,561 | 8/1973 | Wildi et al. ...................... 424/50 |
| 4,150,113 | 4/1979 | Hoogendoorn et al. .......... 424/50 |
| 4,159,317 | 6/1979 | Onisi et al. ....................... 424/50 |
| 4,178,362 | 12/1979 | Hoogendoorn et al. ......... 424/50 |
| 4,246,256 | 1/1981 | Lembke ............................ 424/50 |
| 4,255,414 | 3/1981 | Lembke ............................ 424/50 |
| 4,269,822 | 5/1981 | Pellico et al. ..................... 424/50 |
| 4,335,101 | 6/1982 | Stoudt et al. ..................... 424/50 |
| 4,438,093 | 3/1984 | Shimada et al. .................. 424/50 |
| 4,537,764 | 8/1985 | Pellico et al. ..................... 424/50 |
| 4,564,519 | 1/1986 | Pellico et al. ..................... 424/50 |
| 4,578,265 | 3/1986 | Pellico et al. ..................... 424/50 |

FOREIGN PATENT DOCUMENTS

| | | | |
|---|---|---|---|
| 755331 | 10/1970 | Belgium .............................. | 424/50 |
| 751739 | 11/1970 | Belgium .............................. | 424/50 |
| 756129 | 2/1971 | Belgium .............................. | 424/50 |
| 1467951 | 2/1969 | Fed. Rep. of Germany ........ | 424/50 |
| 467SM | 1/1967 | France ................................ | 424/50 |
| 1031830 | 6/1966 | United Kingdom ................ | 424/50 |
| 1232627 | 5/1971 | United Kingdom ................ | 424/50 |
| 2068730A | 8/1981 | United Kingdom ................ | 424/50 |

*Primary Examiner*—Shep K. Rose
*Attorney, Agent, or Firm*—Arthur L. Plevy

[57] ABSTRACT

This invention is a solid breath cleansing confection and a method for its manufacture which comprises an ingestibly acceptable alpha-amylase of between 1-8 SKB units of alpha-amylase which is in sufficient amount to degrade starch. The alpha-amylase may be from any source but in the currently preferred embodiment it is a fungal alpha-amylase. The confection may further comprise a solid comestible confectionary base containing flavoring and a sweetener which does not promote tooth decay. The sweeteners may be natural or artificial and in the currently preferred embodiment the sweetener is sorbitol. The confectionary base may be a gum or lozenge base and the flavoring may be natural or artificial flavoring, for example, mint flavoring such as natural or artificial wintergreen or natural or artificial spearmint.

20 Claims, No Drawings

AMYLASE CONTAINING BREATH CLEANSING CONFECTION

FIELD OF INVENTION

This invention relates to the field of oral hygiene. More specifically, this invention relates to the field of halitosis prevention.

BACKGROUND OF THE INVENTION

Incomplete mastication of food frequently results in undigested portions of food, termed food debris, remaining in the mouth especially in locations which may easily trap small particles, such as, by example, between teeth. Food debris may then be colonized by bacteria which promote the decay of the food debris and thereby substantially contribute to the cause of bad breath.

Many products are available in the market which purport to remove odors associated with halitosis. These products generally serve to mask the effects of bad breath by imparting a pleasant smell to the breath rather than eliminating the causative factor of bad breath. As such, these products constitute breath sweeteners such as candies, mints, gums, sprays and other various substances and formulations which essentially serve to disguise malodorous breath. Other substances in the market, such as mouthwashes and so on, purport to kill or destroy bacteria and hence to reduce the effects of bad breath by preventing increased rates of food debris putrefaction by bacteria. There is a need for a product which effectively reduces or eliminates odors associated with bad breath at the source of said odors—to wit food debris—in a consistent and reliable manner. The breath cleanser of this invention harnesses the enzymatic reaction of alpha-amylase which breaks down the food debris on which bacteria colonize and thereby prevents increased rates of bacterial putrefaction of food debris and the resultant bad breath.

In spite of conventional oral hygiene procedures, food debris exists in the mouth in varying amounts. The chemical description of the bulk of this debris, at least insofar as it relates to bacterial colonization of the food debris, is starch. Starch occurs in two forms, alpha-amylose and amylopectin. Alpha-amylose is composed of D-glucose monomer units bound in alpha(1→4) linkages. Distinctly, amylopectin, in addition to alpha (1→4) glucose linkages, further comprises glucose chains which branch off the main unbranched alpha(1→4) backbone. The specific branch points which comprise amylopectin are connected to the unbranched glucose backbone by alpha(1→6) linkages. The linkages in the branch itself are thesame alpha(1→4) linkages found in the unbranched glucose chains of amylose.

Amylose can be degraded by a hydrolysis reaction catalyzed by the enzyme alpha(1→4)-glucan 4-glucanohydrolase. This enzyme is commonly referred to by its trivial name alpha-amylase. Alpha-amylase hydrolyzes starch by randomly attacking alpha(1→4) linkages to yield a mixture of glucose and free maltose. (Maltose is a disaccharide composed of two glucose monomers linked together by an alpha(1→4) linkage.) The bacteria which increase the rate of food debris putrefaction primarily colonize that portion of food debris which is amylose. The confection of this invention degrades the amylose through the use of alpha-amylase. As a result, the halitosis causing bacteria are denied a colonizable food source in the mouth.

Use of enzymatic reactions in oral hygiene is known, as evideced by Hoogendorn et al., U.S. Pat. No. 4,178,362. Formulations are extant which add alphaamylase as an ingredient in dentifrice compositions for the prevention of dental caries. See, for example, Iioka et al., U.S. Pat. Nos. 4,469,673; Pader et al., 3,885,142. Some dentifrices use bacterially derived amylases in combination with a protective colloid as in German Pat. No. 1,467,797. All dentifrice compositions using amylase are liquids and, in at least one formulation, flavoring was added British Pat. No. 1,232,627. It is important to emphasize, however, that the use of amylase in dentifrice compositions is directed not towards the elimination of halitosis but as a appropriate chemical mechanism for the prevention of dental caries. More importantly, dentifrice compositions are not designed to be ingested. This non-comestibility is connected to adverse reactions associated with the ingestion of alpha-amylase at the concentrations in which it is found in dentifrice compositions. Among the adverse reactions which are commonplace is gastrointestinal distress. Despite these contraindications, amylase is found in dentifrice compositions because it is well-known that the enzyme will not have a detrimental effect on the organic structure of the mouth itself.

The prophylactic benefit of liquid dentifrices in the prevention of halitosis is severely limited. As noted, dentifrice compositions which contain alpha-amylase can cause gastrointestinal illness if ingested. Additionally, as is well-known, dentifrice prophylaxis requires the brushing of teeth and the tools necessary to accomplish that task, i.e. a toothbrush and potable water, are not always handy. In the minute-to-minute workings of society, the carrying around of a toothbrush and dentifrice, let alone seeking out potable water, is impractical; this accounts for the aforementioned existence of a proliferation of confections which seek to mask the odors caused by halitosis rather than preventing the formation of odors at their source. The instant invention attacks the problem of halitosis at its cause by enzymatically changing the food debris in the mouth using alpha-amylase in appropriate amounts to avoid any contraindications and, thereby, limit bacterial putrefaction and its concomimitant bad odors.

SUMMARY OF THE INVENTION

This invention is a solid breath cleansing confection which comprises an ingestibly acceptable alpha-amylase of between 1-8 SB units of alpha-amylase which is in sufficient amount to degrade starch. The alpha-amylase may be from any source but in the currently preferred embodiment it is a fungi alpha-amylase. The confection may further comprise a solid comestible confectionary base containing flavoring and a sweetener which does not promote tooth decay. The sweeteners may be natural or artificial and in the currently preferred embodiment the sweetener is sorbitol. The confectionary base may be a gum or lozenge base and the flavoring may be natural or artificial flavoring, for example, mint flavoring such as natural or artificial wintergreen, peppermint and so on.

This invention is also a method for the degradation of starch to decompose food debris through the manufacture of a solid breath cleansing confection. This method comprises the steps of taking an appropriate amount of alpha-amylase, namely between 1-8 SKB units of alpha-amylase, combining the amylase with a sweetener which does not promote tooth decay to provide a sweetened amylase combination; adding a comestible, confectionary base containing flavoring; and thereby, create an amylase containing breath cleansing confection. In the currently most preferred embodiment, the alpha-amylase used is fungal alpha-amylase. The method works equally well with natural or artificial sweeteners such as sorbitol or aspartame, respectively. The confectionary base may be a lozenge or gum base and the flavoring may be, for example, any type of mint flavoring. When manufacturing the breath cleansing confection said confection may further comprise chemicals such as magnesium stearate, povidone, syloid and siliceous earth.

DETAILED DESCRIPTION

Halitosis is a known social problem. As a result, there have been numerous attempts to mitigate the halitosis problem through the use of products which disguise the malodorous scents associated with halitosis by masking said odors with more pleasant scents. The present invention describes a breath cleanser which, while imparting a pleasant scent to the breath, also attacks the cause of halitosis through the enzymatic degradation of food debris.

The elimination of halitosis is accomplished by introducing alpha-amylase into a confection, i.e., a gum base or lozenge base, which can be easily carried by a user. Any alpha-amylase is appropriate for use in this invention so long as it is of an acceptable formulation for human consumption. Among the acceptable sources of alpha-amylase are those that are essentially from pancreatic concentrates of bovine or porcine origin; such products include Pancreatin ® brand amylase manufactured by Eli Lilly and Co. as well as alpha-amylases manufactured by other pharmaceutical companies such as Parke-Davis. However, plant alpha-amylase such as fungal alpha-amylase is equally acceptable. Additionally, amylase sources which are not solely amylase are acceptable such as Pancrease ® brand amylase which is comprised of lipase and amylase.

In accordance with this invention, alpha-amylase is incorporated into single units of a confection in small amylase mini-units of 1–8 SKB (Sandstedite, Kaneen, Blish) units. Use of mini-units of alpha-amylase surprisingly resulted in the cleansing of breath and elimination of halitosis without the gastrointestinal distress normally associated with the ingestion of amylase. Mini-units of amylase may be added to many existing confections which are currently designed simply to mask the odors of halitosis. These mini-units of amylase will be sufficient to cause the breakdown of the starchy food debris in the mouth but impart no adverse or undesirable flavors to the confections, thereby, not necessitating a reformulation of the confection. Nor will the alpha-amylase adversely affect the organic structures of the mouth. Moreover, the cost of alpha-amylase is trivial and would not substantially increase the cost of the confection. Thus, this invention discloses a breath-cleansing confection having the joint properties of imparting a pleasant aroma to the breath and, simultaneously, destroying the food source which permits bacterial putrefaction and the concomitant malodorous scents associated with halitosis.

By this invention it is envisioned that an amylase containing breath cleanser may be solid or liquid but, preferably, it shall be in the form of a solid confection. Such a confection may, of course, take many forms but is most likely to be in the form of a gum or lozenge. The usual materials necessary for the manufacture of said confections will not adversely affect the amylase present in the confection. Specifically, such ingredients as sweeteners and siliceous earth will not adversely affect the amylase.

In order to make the amylase containing breath cleansing confection more palatable and, thus, more likely to be used, it is expected that sweeteners and flavorings will be added to the confection. Since it is the object of this confection to avoid halitosis, it is envisioned that easily purtrefiable sugars which cause tooth decay such as simple glucose are not to be the sweeteners of choice. Of course, it is understood that the breath cleansing confection will work equally well with all sweeteners including glucose and artificial sweeteners such as aspartame. Moreover, as previously mentioned, any flavoring, for instance natural or artificial wintergreens and spearmints, may be added to the confection to impart a distinctive flavor to the confection. The addition of sweetener or flavoring will be as desired but, most preferably, the confection shall contain a large portion of sweetener, well in excess of 50% of ingredients, and a small quantity of flavoring as needed. Most specifically, the breath cleansing confection may comprise in excess of 90% sweetener and less than 5% of all other ingredients such as, by example, flavoring and most inert ingredients such as syloid, siliceous earth, magnesium stearate and povidone.

A method of manufacturing an amylase containing solid breath cleansing confection was also invented. This method comprises the use of between 1-8 SKB units of alpha-amylase, combining said amylase with a natural or artificial sweetener which does not promote tooth decay and adding this combination to a comestible, confectionary base containing flavoring if desired. Similar to the breath cleansing confection, the alphaamylase may be any amylase of plant of animal origin but it is most preferred to be fungal alpha-amylase. Any natural or artificial sweetener is appropriate such as sorbitol or aspartame respectively. Similarly, any flavoring would be acceptable; most preferred is mint flavoring.

It is most expected that the comestible, confectionary base will be in a solid phase and likely in a gum or lozenge base. Various chemicals and inert ingredients may be added during the manufacture of the amylase containing confection such as magnesium stearate, povidone, syloid and siliceous earth.

EXAMPLE

The breath-cleansing confection of this invention has been formulated in a lozenge base. This lozenge is comprised of 450 milligrams sorbitol, N.F.; 5 milligrams magnesium stearate, USP; 5 milligrams povidone USP; 5 milligrams syloid, F.C.C.; 5 millirams siliceous earth, N.F.; Q.S. natural and artificial wintergreen flavor; and 1-8 SKB units fungal alpha-amylase.

I claim:

1. A breath cleansing confection comprisng a solid confectionary base consisting essentially of an ingestibly acceptable alpha-amylase in sufficient amount, namely not to exceed about 8 SKB units of said amylase, to degrade starch as present in food debris within a user's mouth, while avoiding gastrointestinal illness.

2. The confection of claim 1 wherein said alpha-amylase is fungal alpha-amylase.

3. The confection of claim 1 further comprising a solid, comestible, confectionary base containing flavoring and sweetener other than glucose.

4. The confection of claim 3 wherein said confectionary base is a gum base.

5. The confection of claim 3 wherein said confectionary base is lozenge base.

6. The confection of claim 5 wherein said confectionary base comprises approximately 96% sorbitol, 1% magnesium stearate, 1% povidone, 1% syloid, 1% siliceous earth.

7. The confection of claim 3 wherein the flavoring is mint flavoring.

8. The confection of claim 7 wherein said mint flavoring in wintergreen.

9. The confection of claim 3 wherein said flavoring is selected from the group consisting of natural wintergreen, artificial wintergreen, natural spearming or artificial spearmint, natural or artificial peppermint.

10. The confection of claim 3 wherein said confectionary base is comprised primarily of a sweetener whereby said sweetener does not promote tooth decay.

11. The confection of claim 10 wherein said sweetener is sorbitol.

12. A method for the degradation of starch to decompose food debris present in the mouth of a user through the manufacture of a breath cleansing confection while avoiding gastrointestinal illness comprising the steps of: using mini-units of amylase in solid confectionary base in the mouth, in amounts sufficient to cause the breakdown of halitosis—causing starchy food debris in the mouth, each of said mini-units having been prepared by the process of:
   (a) combining not more than 1–8 SKB units of alpha-amylase with a sweetener to provide a sweetened, amylase combination;
   (b) adding a solid comestible, confectionary base to said combination to thereby, create an amylase containing breath cleansing confection.

13. The method of claim 12 wherein said alpha-amylase is fungal alpha-amylase.

14. The method of claim 12 wherein said sweetener is sorbitol.

15. The method of claim 12 wherein said sweetener is aspartame.

16. The method of claim 12 wherein said comestible, confectionary base is in a solid phase.

17. The method of claim 16 wherein said solid, comestible, confectionary base is a lozenge base.

18. The method of claim 16 wherein said solid, comestible, confectionary base is a gum base.

19. The method of claim 16 wherein the manufacture of the solid breath cleansing confection further comprises mixing magnesium stearate, povidone, syloid and siliceous earth.

20. The method of claim 12 wherein said flavoring is mint flavoring.

* * * * *